United States Patent
Graumann et al.

(10) Patent No.: US 9,782,143 B2
(45) Date of Patent: Oct. 10, 2017

(54) CONTROL UNIT AND METHOD FOR CONTROLLING A MOBILE MEDICAL DEVICE

(71) Applicant: SIEMENS AKTIENGESELLSCHAFT, Munich (DE)

(72) Inventors: Rainer Graumann, Hoechstadt (DE); Sorin-Alexandru Neagu, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 835 days.

(21) Appl. No.: 13/803,607

(22) Filed: Mar. 14, 2013

(65) Prior Publication Data
US 2013/0243160 A1    Sep. 19, 2013

(30) Foreign Application Priority Data
Mar. 14, 2012 (DE) ............. 10 2012 204 018

(51) Int. Cl.
*A61B 6/00* (2006.01)

(52) U.S. Cl.
CPC .............. *A61B 6/54* (2013.01); *A61B 6/4405* (2013.01); *A61B 6/4441* (2013.01); *A61B 6/467* (2013.01)

(58) Field of Classification Search
CPC ......... A61B 6/4441; A61B 6/467; A61B 6/54; G05D 1/0044; G05D 1/0016; G05D 1/0033; G06F 3/0489; G06Q 10/02; H01M 10/0525; H01M 10/058; H01M 2004/021; H01M 2/26; H01M 4/0404; H01M 4/0416; H01M 4/043; H01M 4/131
See application file for complete search history.

(56) References Cited

U.S. PATENT DOCUMENTS

| | | | |
|---|---|---|---|
| 6,149,674 A | 11/2000 | Borders | |
| 2008/0013692 A1* | 1/2008 | Maschke | 378/198 |

(Continued)

FOREIGN PATENT DOCUMENTS

| | | |
|---|---|---|
| CN | 102006828 A | 4/2011 |
| DE | 19520170 A1 | 5/1996 |

(Continued)

OTHER PUBLICATIONS

Kartoun et al., "Tele-Control of a Mobile Robot Using Touch Screen Interface", Available on line Aug. 1, 2007, retrieved from Internet: https://www.youtube.com/watch?v=4sxHRVvHoll, Ben Gurion University of Negev, see attached screenshots, 6 pages.*

(Continued)

*Primary Examiner* — Glen Kao
(74) *Attorney, Agent, or Firm* — Laurence Greenberg; Werner Stemer; Ralph Locher

(57) ABSTRACT

A medical device, such as a mobile C-arm, is positioned and/or aligned via a touch-sensitive control panel of a tablet. The touch-sensitive control panel provides access to one or more function units, for example, for initiating control signals for a positioning and/or an alignment of the medical device, or a second function unit for specifying a direction of movement for a mobile medical unit, or a third function unit for specifying a motion speed for the mobile medical device.

5 Claims, 2 Drawing Sheets

(56) References Cited

U.S. PATENT DOCUMENTS

| | | |
|---|---|---|
| 2008/0069309 A1 | 3/2008 | Dorre |
| 2010/0299014 A1* | 11/2010 | Bouvier ............... A61B 6/4405 |
| | | 701/25 |
| 2010/0321324 A1 | 12/2010 | Fukai et al. |
| 2011/0082395 A1 | 4/2011 | Burkhardt et al. |
| 2012/0079421 A1* | 3/2012 | Arriola ........................ 715/784 |
| 2012/0188187 A1 | 7/2012 | Doerre et al. |
| 2013/0109272 A1* | 5/2013 | Rindlisbacher ............... 446/454 |

FOREIGN PATENT DOCUMENTS

| | | |
|---|---|---|
| DE | 69822188 T2 | 7/2004 |
| DE | 102008050542 A1 | 4/2010 |
| DE | 102009036941 A1 | 2/2011 |

OTHER PUBLICATIONS

Siemens ("Artis zee floor/biplane, Quick reference guide vol. 1", Mar. 9, 2012, document No. AXA4-100.622.18.01.02, available at http://abimo.org.br/uploads/servicos/similar/1445275216834cd915d9871e3d6502c623e0d.pdf.*

* cited by examiner

CONTROL UNIT AND METHOD FOR CONTROLLING A MOBILE MEDICAL DEVICE

CROSS-REFERENCE TO RELATED APPLICATION

This application claims the priority, under 35 U.S.C. §119, of German patent application DE 10 2012 204 018.8, filed Mar. 14, 2012; the prior application is herewith incorporated by reference in its entirety.

BACKGROUND OF THE INVENTION

Field of the Invention

The invention relates to an apparatus and an associated method for controlling a medical device.

Mobile x-ray devices are moved toward the operating table in order to record x-ray images of the treatment area on the patient prior to and/or during as well as after an operative intervention. In order to obtain free access to the working area adjacent to the operating table, a mobile C-arm is frequently moved back into a parking position away from the operating table following each recording or each recording cycle. A repositioning of the mobile C-arm for instance adjacent to the operating table requires an increased time outlay since minimal changes in position out of a plurality of possible directions of movement are to be implemented here until a position and/or alignment is reached.

SUMMARY OF THE INVENTION

It is accordingly an object of the invention to provide a method and a control unit that overcome a variety of disadvantages of the heretofore-known devices and methods of this general type and which provides for an improved novel apparatus and an associated method for controlling a medical device.

With the foregoing and other objects in view there is provided, in accordance with the invention, an apparatus for controlling a mobile medical device, the apparatus comprising:

a tablet computer configured for controlling a movement of the mobile medical device;

said tablet computer having a touch-sensitive control panel; and said control panel of a control unit of said tablet computer having at least one function unit for initiating control signals for a positioning and/or an alignment of the medical device.

In other words, according to the invention, the apparatus and the associated method utilize, a tablet PC with a touch-sensitive control panel for motion control of a mobile medical device, wherein the tablet PC has a control unit with at least one function unit for initiating control signals for a positioning and/or alignment of the medical device.

The invention is advantageous in that the C-arm can be moved into a specific position and/or alignment without any physical effort.

The invention is advantageous in that the position and alignment of the C-arm can be stored.

The invention is advantageous in that the controls in respect of the direction and motion and/or rotational speed of the motorized drive means of the C-arm are implemented by means of control signals which are initialized by a touch-sensitive operating interface of a tablet PC.

The invention is advantageous in that parking positions of the C-arm or positions of the C-arm can be stored for instance and repositioned again there with a selection menu and marking or navigation aids.

The invention is advantageous in that the direction of movement of the mobile C-arm is derived from a first starting point and a target location set or a path drawn by means of an auxiliary means or finger on the operating interface of the tablet PC, and control signals for a direction of movement are calculated therefrom.

In accordance with an added feature of the invention, the motion speed of the mobile C-arm is derived from the length of the direction vector.

In accordance with an added feature of the invention, when contact with the operating interface of the tablet PC is stopped in a computing unit assigned hereto, control signals for stopping the mobile C-arm are initialized.

The invention is advantageous in that after actuating a function field to be actuated for a repositioning of the mobile C-arm, control signals are initiated to control the mobile C-arm.

The invention is advantageous in that a parallel displacement of the mobile C-arm relative to the operating table for instance is implemented by means of two touch points on the operating interface of the tablet PC.

The invention is advantageous in that the tablet PC can also be operated by persons wearing sterile gloves.

Other features which are considered as characteristic for the invention are set forth in the appended claims.

Although the invention is illustrated and described herein as embodied in a control unit and a method, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

The following description of an exemplary embodiment details a positioning and/or alignment of a mobile device, in particular a C-arm, by way of a touch-sensitive control panel with the present apparatus and the associated method.

Figure 1:
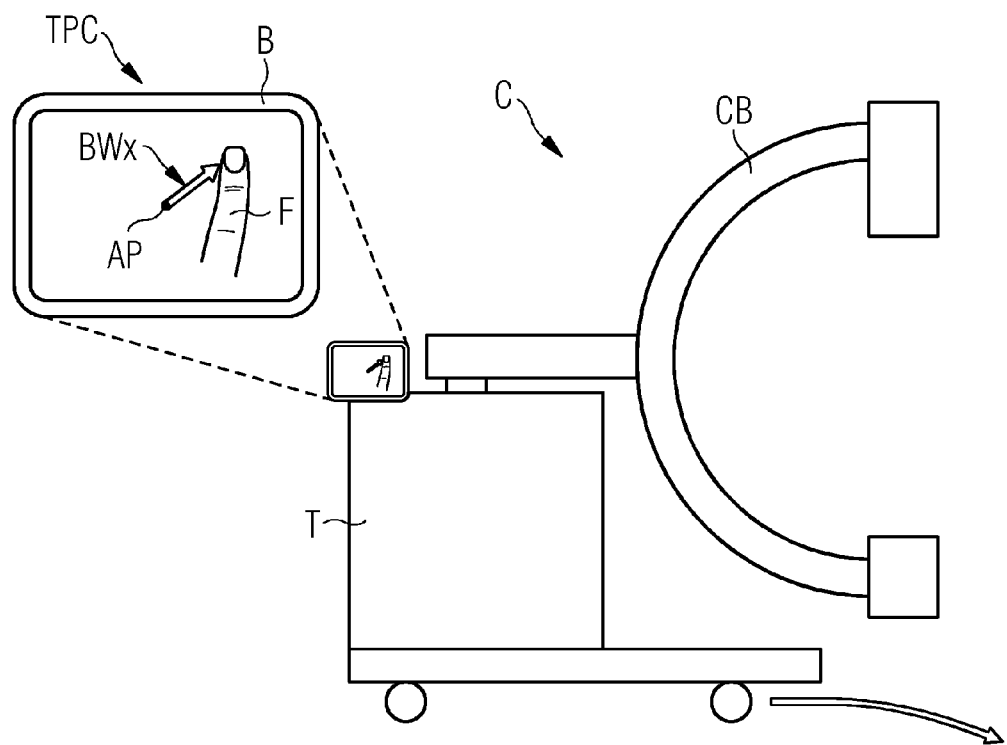
FIG. 1 is a diagrammatic side view of an arrangement of the control panel on a medical device.

Referring now to the figures of the drawing in detail and first, particularly, to FIG. 1 thereof, there is shown a medical device C, in particular a mobile C-arm, with a control unit B. The control unit B, for instance in the embodiment of a tablet PC (TPC), is positioned in this representation on the front face of a chassis T of the mobile C-arm C. The tablet computer TPC, or tablet for short, can be arranged variably on the chassis of the medical device. The control unit B can be aligned arbitrarily by a user using a ball joint with a telescopic stand, so that it is possible to optimize control for a user. The control panel is divided into a plurality of selectable function units comprising functions. The individually adjustable functions are selected by a contact with the display and/or user interface GUI of the control panel BF of the control unit B. The user interface may be a touchscreen, so that contact with the user interface can be effected by way of a finger or any rod-shaped auxiliary means F, e.g., a stylus. The computing operations needed to navigate the mobile C-arm in order to generate control signals for the motorized units are implemented in the tablet TPC itself or in the computing unit that is arranged in the chassis of the mobile C-arm. The computing operations are implemented in order to form both the necessary control signals to move the drive means of the chassis about the mobile C-arm and also the control signals to set the angulation and/or orbital angle A, O of the C-arm. Activation of the individual drive means is started in each instance by tapping the function fields in the function units FE1, . . . , FE8 on the control panel BF of the tablet TPC. A semicircular pivoting S of the C-arm CB is possible (cf. FIG. 2).

Figure 2:
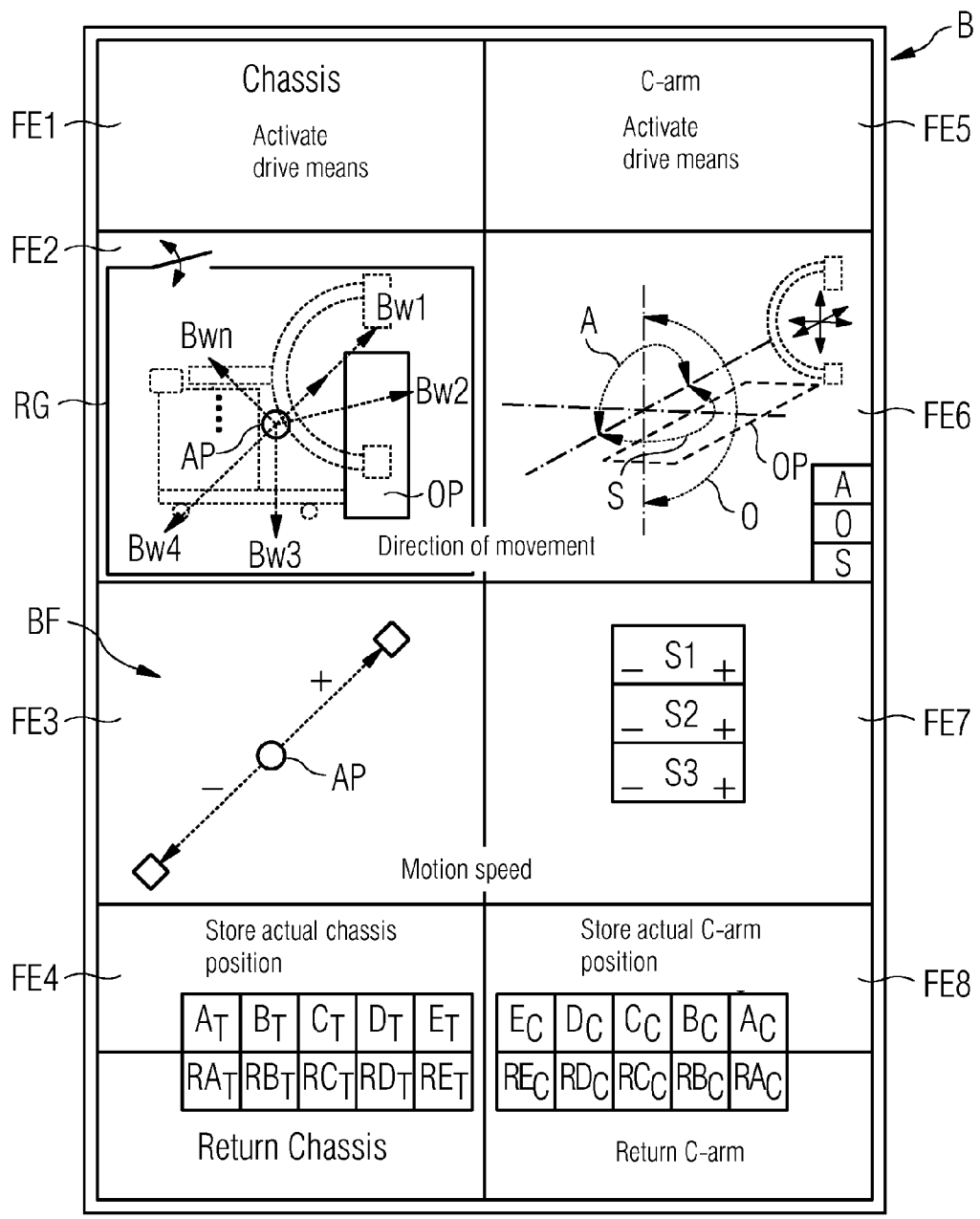
FIG. 2 is a view of a menu screen of the controller GUI.

The control panel BF of the control unit B is reproduced in FIG. 2. This control panel BF is subdivided into a plurality of function units FE1, . . . , FE8 comprising function fields. Specific functions can be called up in each instance by touching the function fields. The function units FE1, . . . , FE8 are reproduced in their entirety. The individual function units FE1, . . . , FE8 may occupy the entire control panel BF or a large part thereof respectively. With a first and fifth function unit FE1, FE5, the drive means are activated in the chassis T or on the C-arm CB. The direction of movement for the chassis T or the C-arm CB is set with a second and sixth function unit FE2, FE6. The motion speed and/or rotational speed is predetermined in each instance with a third and seventh function unit FE3, FE7 and positions of the chassis and the deflections of the C-arm CB are stored for a possible repositioning with a fourth and eighth function unit FE4, FE8. For improved orientation, an outline with possible device objects is superimposed in the control panel of the second function unit FE2 and a possible operating table OP is superimposed in the control panel of the sixth function unit FE6.

Based on the representation of the GUI shown, the control is subdivided into control of the chassis T and control of the C-arm CB. The chassis T is controlled in the left half and the C-arm CB is controlled in the right half of the control panel BF of the control unit B.

A positioning or repositioning of the chassis T begins with an activation of the drive means by way of touching the function fields of the first function unit FE1. If the chassis T, in other words the entire medical unit C, is to be moved, the user therefore for instance touches a first starting point AP defined as a function field in the second function unit FE2 with the finger. The direction in which the chassis T is to be moved is predetermined by tapping a location within a mapped spatial outline RG. A plurality of directions of movement BW1, BW2, BW3, . . . , BWn are indicated. The representation shown with the first starting point AP provides a top view and the current location of the medical unit C within the spatial outline RG of the operating room. An operating table OP is indicated in this operating room. The function field is stored schematically with a side view of the respective medical device. If the direction of movement is reproduced on the display of the tablet PC in the form of a direction vector BWx, the motion speed can be specified to the drive means by means of the third function unit FE3 by means of control signals and/or by applying a supply voltage. This specification takes place by touching the third function unit FE3. Based on the direction vector BWx which is formed based on the first starting point AP relative to the target point, a variation in the motion speed for the chassis can take place by lengthening or shortening the indicated direction vector BWx. A possible backward direction of movement is indicated with – and a forward direction of movement is indicated with + in the control panel. A lengthening of the direction vector results in an increase in the speed of travel and/or a shortening of the direction vector results in a reduction in the speed of travel. During the movement of the chassis T, the finger or the auxiliary means remain in contact with the interface of the control panel BF. If the contact with the interface of the control unit B remains at the same distance from the starting point AP, the speed remains constant. If the forefinger moves on a circular path about the first starting point AP, the current direction of movement changes while retaining the speed. The setting of the speed can also be specified by way of a scale superimposed on the control panel B with possible speed details. The change in direction is achieved by changing the direction vector BWx. If contact with the interface of the tablet PC is interrupted, the chassis stops. The chassis also stops in the event of an imminent collision of the medical device C with possible objects disposed in its movement corridor. A corresponding signaling to the computing unit takes place by means of movement detectors. If the chassis T has reached its destination point, the actual position can be stored. The actual position is recorded for instance by optical or electromagnetic detectors and is converted into navigation data for the mobile unit in a computing unit assigned to the tablet PC. A plurality of actual positions AT, BT, CT, DT, . . . can be stored in each instance in the fourth function field FE4. If a position of the mobile C-arm C for instance adjacent to the operating table OP is to be reassumed after a parking position, this can be moved again by actuating an associated return key RAT, . . . , RET. If the route is in the meantime blocked by an object, a diversion is offered to the operator and shown on the display.

For an alignment of the C-arm CB the function units FE5, . . . , FE8 are reproduced on the right side of the control unit B shown in FIG. 2. After activation, function fields of the sixth function unit FE6 are selected by tapping the operating interface BF. By means of the sixth function unit FE6 the orbital angle O and/or angulation angle A or a pivoting S of the C-arm are selected. Based on an idle position or the current position of the C-arm, the desired angle can be predetermined after superimposing a circle with angular details by touching the same with a forefinger or another cylindrical, pin-type auxiliary means. When the entry is finished, the C-arm pivots in the desired alignment by specifying a rotational speed S1, S2, S3 which can be predetermined by means of the function fields in the function unit FE7. A lower rotational speed can be selected with S1 and a higher rotational speed can be selected with S3. A rotational clockwise movement is shown with Sx+. If contact with the control panel is stopped, then the movement of the C-arm CB stops. A reversal of the direction of movement is shown with –Sx on the function field. An end position can be stored by storing the angular data for a subsequent repositioning Ac, . . . , Ec; RAc, . . . , REc of the C-arm in the eighth function unit FE8.

The mobile C-arm can be shown on the control panel BF as a point, icon or with a perspective representation. If the mobile medical device C is to be moved after activation of the drive means, the interface of the touch screen is touched with a pin-type auxiliary means. Based on the first starting point AP relative to a touch point, the tablet PC calculates the direction vector BWx. The direction, the direction of movement of the mobile device C on the one hand and also the speed on the other hand can be predetermined by way of the input direction vector BWx and the length of the direction vector respectively. A parallel displacement of the mobile C-arm C, for instance relative to the operating table OP, can be implemented by means of two touch points on the operating interface of the tablet PC. The maximum speed for the mobile device C can be predetermined with the third function unit FE3. The mobile device C also has collision vectors, from which control signals are generated for stopping the device if an obstacle was selected. The position of the mobile device within a room can be determined by means of electromagnetic sensors or an ultrasound sensor system for instance. These coordinates can be stored by actuating a function key mapped in the fourth and eighth function unit FE4, FEB. If an idle position is reached for the medical device C, the location can be stored by tapping an idle position key. If the mobile C-arm C is required again adjacent to the operating table for a further x-ray recording for instance, an already defined target point can be automatically reached again by activating the drive means and actuating a return key RAT, . . . , RET; . . . , REC.

The invention claimed is:

1. An apparatus for controlling a mobile medical device including a C-arm, the apparatus comprising:
   a tablet computer configured for controlling a movement of the mobile medical device;
   said tablet computer having a touch-sensitive control panel; and
   said touch-sensitive control panel of a control unit of said tablet computer having a plurality of function units;
   a motorized drive moving said mobile medical device or a component thereof to an actual position or an actual alignment based on input to said touch-sensitive control panel;
   a memory storing at least one of the actual position and the actual alignment of the mobile medical device or a component thereof in response to an input made on said touch-sensitive control panel, and said control panel is operable to reposition said mobile medical device or component thereof to said stored actual position or actual alignment in response to a menu selection made on the touch-sensitive control panel;
   said plurality of function units including:
      a first function unit for initiating control signals for a positioning and/or an alignment of the medical device;
      a second function unit for specifying a direction of movement for the mobile medical device wherein, based on a first starting point and a contact point on the interface of said control panel, a direction vector is formed and direction control signals for a drive of the mobile medical device are derived; and
      a third function unit for specifying a motion speed for the mobile medical device, wherein the motion speed for the mobile medical device is derived from a predetermined length of the direction vector based on the first starting point while retaining the direction of the direction vector, wherein a starting speed is predetermined for an existing length and the starting speed is increased or decreased by lengthening or shortening the direction vector.

2. The apparatus according to claim 1, wherein said plurality of function units includes a fourth function unit for specifying an alignment of the C-arm, wherein directions of movement are selected for the C-arm and an angular setting can be predetermined.

3. The apparatus according to claim 1, wherein the mobile medical device is a mobile C-arm and said plurality of function units includes a fourth function unit for specifying a rotational speed for the C-arm.

4. A method of controlling a mobile medical device including a C-arm, the method which comprises:
   providing a tablet computer with a touch-sensitive control panel and a control unit configured to control the mobile medical device or a component thereof;
   the touch-sensitive control panel of the control unit having a plurality of function units, including at least a first function unit, a second function unit, and a third function unit;
   initiating with the first function unit of the touch-sensitive control panel of the control unit control signals for a positioning and/or an alignment of the mobile medical device;
   specifying with the second function unit a direction of movement of the mobile medical device by defining a starting point and a contact point on touch-sensitive control panel, thereby forming a direction vector between the starting point and the contact point and generating corresponding control signals for a drive of the mobile medical device;
   specifying with the third function unit a motion speed for the mobile medical device, wherein a starting speed is derived from a predeterminable length of the direction vector based on the starting point while retaining the direction of the direction vector, and wherein the starting speed is predetermined for an existing length of the direction vector and the starting speed is increased or decreased by lengthening or shortening the direction vector;
   moving the mobile medical device or component thereof to an actual position or an actual alignment, in response to the first, second and third function units specified using the touch-sensitive control panel;
   storing the actual position or actual alignment of the mobile medical device or component thereof in a memory of the tablet computer; and
   repositioning the mobile medical device or component thereof to the stored actual position or stored actual alignment in response to a menu selection made on the touch-sensitive control panel.

5. The method according to claim 4, wherein the method comprises selecting a motion direction for the C-arm and predetermining an angular setting and a rotational speed thereof.

* * * * *